(12) United States Patent
Shute et al.

(10) Patent No.: US 11,246,537 B2
(45) Date of Patent: Feb. 15, 2022

(54) SIGNAL AMPLITUDE CORRECTION USING SPATIAL VECTOR MAPPING

(71) Applicant: Cardiac Pacemakers, Inc., St. Paul, MN (US)

(72) Inventors: Jonathan B. Shute, Minnetonka, MN (US); Kyle H. Srivastava, St. Paul, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 363 days.

(21) Appl. No.: 16/261,811

(22) Filed: Jan. 30, 2019

(65) Prior Publication Data

US 2019/0231273 A1 Aug. 1, 2019

Related U.S. Application Data

(60) Provisional application No. 62/625,264, filed on Feb. 1, 2018.

(51) Int. Cl.
| | |
|---|---|
| *A61B 5/00* | (2006.01) |
| *G16H 50/30* | (2018.01) |
| *A61B 5/11* | (2006.01) |
| *G16H 10/60* | (2018.01) |
| *G16H 40/60* | (2018.01) |

(52) U.S. Cl.
CPC .......... *A61B 5/7203* (2013.01); *A61B 5/1102* (2013.01); *A61B 5/1112* (2013.01); *A61B 5/1113* (2013.01); *A61B 5/1116* (2013.01); *A61B 5/1118* (2013.01); *A61B 5/7275* (2013.01); *G16H 10/60* (2018.01); *G16H 40/60* (2018.01); *G16H 50/30* (2018.01); *A61B 2562/0219* (2013.01)

(58) Field of Classification Search
CPC ... A61B 5/1102; A61B 5/7275; A61B 5/0205; A61B 5/024
USPC .......................... 600/300, 301, 513, 527, 528
See application file for complete search history.

(56) References Cited

U.S. PATENT DOCUMENTS

| | | | |
|---|---|---|---|
| 7,123,954 B2 | 10/2006 | Narayan et al. | |
| 7,458,939 B2 | 12/2008 | Munk | |
| 8,209,002 B2 * | 6/2012 | Vajdic | A61B 5/349 600/512 |
| 2006/0161070 A1 * | 7/2006 | Siejko | A61B 5/1107 600/528 |

(Continued)

FOREIGN PATENT DOCUMENTS

WO 2014182822 A1 11/2014

*Primary Examiner* — John R Downey
(74) *Attorney, Agent, or Firm* — Faegre Drinker Biddle & Reath LLP

(57) ABSTRACT

A system includes a sensor configured to sense first and second physiological signals produced by a source; and a processing device communicatively coupled to the sensor. The processing device is configured to: receive the first and second physiological signals; determine a first value of a signal characteristic; determine a second value of the signal characteristic; access a scaling map having scaling vectors, and each scaling vector having at least one signal characteristic correction value; determine a scaled first value and a scaled second value based on a first scaling vector and a second scaling vector, respectively; and predict a physiological event based on the scaled first value of the signal characteristic and the scaled second value of the signal characteristic.

20 Claims, 6 Drawing Sheets

(56) References Cited

U.S. PATENT DOCUMENTS

| | | | |
|---|---|---|---|
| 2009/0264778 A1* | 10/2009 | Markowitz | A61B 5/053 600/508 |
| 2015/0126820 A1* | 5/2015 | Muhlsteff | A61B 5/0205 600/301 |
| 2016/0007935 A1* | 1/2016 | Hernandez | A61B 5/6814 600/301 |
| 2016/0135706 A1* | 5/2016 | Sullivan | A61N 1/0484 600/301 |
| 2016/0296159 A1* | 10/2016 | Larson | A61B 5/746 |
| 2019/0083039 A1* | 3/2019 | Shute | A61B 5/0205 |
| 2019/0365290 A1* | 12/2019 | Lee | A61B 5/1116 |

\* cited by examiner

SIGNAL AMPLITUDE CORRECTION USING SPATIAL VECTOR MAPPING

CROSS-REFERENCE TO RELATED APPLICATION

This application claims priority to Provisional Application No. 62/625,264, filed Feb. 1, 2018, which is herein incorporated by reference in its entirety.

TECHNICAL FIELD

The presently disclosed subject matter relates to devices and methods for monitoring a subject's health using one or more medical devices. More specifically, the disclosed subject matter relates to devices, systems, and methods for correcting physiological signal characteristics used to facilitate physiological event prediction and intervention.

BACKGROUND

The opening and closing of valves, as well as aspects of the flow of blood through the heart, produce acoustic and/or vibratory physiological signals known as heart sounds (sometimes abbreviated as "HS" herein). Heart sounds may be measured and used, for example, to indicate the heart's mechanical activities. Heart sounds may, for example, reveal signs of elevated filling pressure, weakened ventricular contraction, and/or the like. Heart sounds (e.g., S1 and/or S3) may be used as part of a predictive algorithm configured to predict physiological events.

Additionally, the inventors have found that the largest source of variability between heart sound signal characteristic values between different medical devices is the location of the medical device with respect to the source of the heart sounds. Obtaining physiological signals (e.g., heart sounds) from multiple locations, using one or more medical devices, may facilitate more accurate heart sounds identification and, thus, may facilitate more accurate prediction of physiological events.

SUMMARY

Embodiments disclosed herein use a scaling map to correct heart sounds measurements used in a predictive algorithm. Example embodiments include, but are not limited to, the following examples.

In an Example 1, a system for facilitating physiological monitoring, the system comprising: at least one sensor configured to sense (1) a first physiological signal, at a first location, produced by a source, wherein the source is associated with a body part of a subject, and (2) a second physiological signal, at a second location, produced by the source; and at least one processing device communicatively coupled to the at least one sensor, the at least one processing device configured to: receive the first and second physiological signals; determine a first value of a signal characteristic, the first value of the signal characteristic corresponding to the first physiological signal; determine a second value of the signal characteristic, the second value of the signal characteristic corresponding to the second physiological signal; access a scaling map, the scaling map comprising a plurality of scaling vectors, each of the plurality of scaling vectors corresponding to one of a plurality of locations, the plurality of locations comprising the first location and the second location, and each scaling vector comprising at least one signal characteristic correction value; determine a scaled first value and a scaled second value based on a first scaling vector and a second scaling vector, respectively, the first scaling vector corresponding to the first location and the second scaling vector corresponding to the second location; and predict a physiological event based on the scaled first value of the signal characteristic and the scaled second value of the signal characteristic.

In an Example 2, the system of Example 1, wherein the at least one sensor comprises an accelerometer configured to sense an acceleration signal produced by the source.

In an Example 3, the system of either of Examples 1 or 2, wherein the source is a heart of the subject, and wherein the acceleration signal corresponds to one or more heart sounds.

In an Example 4, the system of any of Examples 1-3, wherein the signal characteristic comprises at least one of an amplitude, a phase, and a frequency.

In an Example 5, the system of any of Examples 1-4, wherein the scaling map is associated with a first state and an additional scaling map is associated with a second state, the at least one processing device being further configured to: determine that the subject is in the first state; and select the scaling map in response to determining that the subject is in the first state.

In an Example 6, the system of Example 5, wherein the first state corresponds to a first value of a state parameter, the state parameter comprising at least one of a position of the subject, a posture of the subject, an activity of the subject, and a location of the subject.

In an Example 7, the system of any of Examples 1-6, wherein the first scaled value and the second scaled value are determined by applying a linear normalization based on the first scaling vector and the second scaling vector, respectively.

In an Example 8, The system of any of Examples 1-7, wherein the at least one processing device is configured to predict the physiological event by applying a predictive model that was created based on one or more observations associated with a reference location, and wherein the at least one processing device is configured to create the scaling map by: determining a linear normalization associated with a plurality of signal characteristic values, the plurality of signal characteristic values comprising at least the first value of the signal characteristic and the second value of the signal characteristic; identifying a location of the plurality of locations that corresponds to the reference location; and projecting the linear normalization into a reference position space corresponding to the reference location.

In an Example 9, the system of any of Examples 1-8, wherein the at least one processing device is configured to create the scaling map based on at least a third physiological signal and a fourth physiological signal, wherein the third physiological signal corresponds to the first location, and wherein the fourth physiological signal corresponds to the second location.

In an Example 10, a method for facilitating physiological monitoring, the method comprising: receiving, from at least one sensor at a first location, a first physiological signal produced by a source, wherein the source is associated with a body part of a subject; receiving, from the at least one sensor at a second location, a second physiological signal produced by the source; determining a first value of a signal characteristic, the first value of the signal characteristic corresponding to the first physiological signal; determining a second value of the signal characteristic, the second value of the signal characteristic corresponding to the second physiological signal; accessing a scaling map, the scaling map comprising a plurality of scaling vectors, each of the plurality of scaling vectors corresponding to one of a plurality of locations, the plurality of locations comprising the first location and the second location, and each scaling vector comprising at least one signal characteristic correction value; determining a scaled first value and a scaled second value based on a first scaling vector and a second scaling vector, respectively, the first scaling vector corresponding to the first location and the second scaling vector corresponding to the second location; and predicting a physiological event based on the scaled first value of the signal characteristic and the scaled second value of the signal characteristic.

In an Example 11, the method of Example 10, wherein the first sensor comprises an accelerometer configured to sense an acceleration signal produced by the source.

In an Example 12, the method of either of Examples 10 or 11, wherein the source is a heart of the subject, and wherein the acceleration signal corresponds to one or more heart sounds.

In an Example 13, the method of any of Examples 10-12, wherein the signal characteristic comprises at least one of an amplitude, a phase, and a frequency.

In an Example 14, the method of any of Examples 10-13, wherein the at least one processing device is configured to create the scaling map based on at least a third physiological signal and a fourth physiological signal, wherein the third physiological signal corresponds to the first location, and wherein the fourth physiological signal corresponds to the second location.

In an Example 15, One or more computer-readable media having computer-executable instructions embodied thereon that, when executed by at least one processing device, are configured to cause the at least one processing device to perform a method of facilitating physiological monitoring, the method comprising: receiving, from a first sensor disposed at a first location, a first physiological signal produced by a source, wherein the source is associated with a body part of a subject; receiving, from a second sensor disposed at a second location, a second physiological signal produced by the source; determining a first value of a signal characteristic, the first value of the signal characteristic corresponding to the first physiological signal; determining a second value of the signal characteristic, the second value of the signal characteristic corresponding to the second physiological signal; creating, based on the first and second signal characteristics, a scaling map, the scaling map comprising a plurality of scaling vectors, each of the plurality of scaling vectors corresponding to one of the plurality of locations, each scaling vector comprising at least one signal characteristic correction value; receiving, from the first sensor, a third physiological signal; receiving, from the second sensor, a fourth physiological signal; determining a third value of the signal characteristic, the third value of the signal characteristic corresponding to the third physiological signal; determining a fourth value of the signal characteristic, the fourth value of the signal characteristic corresponding to the fourth physiological signal; accessing the scaling map; determining a scaled third value and a scaled fourth value based on a first scaling vector and a second scaling vector, respectively, the first scaling vector corresponding to the first location and the second scaling vector corresponding to the second location; and predicting a physiological event based on the scaled third value of the signal characteristic and the scaled fourth value of the signal characteristic.

In an Example 16, a system for facilitating physiological monitoring, the system comprising: at least one sensor configured to sense (1) a first physiological signal, at a first location, produced by a source, wherein the source is associated with a body part of a subject, and (2) a second physiological signal, at a second location, produced by the source; and at least one processing device communicatively coupled to the at least one sensor, the at least one processing device configured to: receive the first and second physiological signals; determine a first value of a signal characteristic, the first value of the signal characteristic corresponding to the first physiological signal; determine a second value of the signal characteristic, the second value of the signal characteristic corresponding to the second physiological signal; access a scaling map, the scaling map comprising a plurality of scaling vectors, each of the plurality of scaling vectors corresponding to one of a plurality of locations, the plurality of locations comprising the first location and the second location, and each scaling vector comprising at least one signal characteristic correction value; determine a scaled first value and a scaled second value based on a first scaling vector and a second scaling vector, respectively, the first scaling vector corresponding to the first location and the second scaling vector corresponding to the second location; and predict a physiological event based on the scaled first value of the signal characteristic and the scaled second value of the signal characteristic.

In an Example 17, the system of Example 16, wherein the at least one sensor comprises an accelerometer configured to sense an acceleration signal produced by the source.

In an Example 18, the system of Example 16, wherein the source is a heart of the subject, and wherein the acceleration signal corresponds to one or more heart sounds.

In an Example 19, the system of Example 16, wherein the signal characteristic comprises at least one of an amplitude, a phase, and a frequency.

In an Example 20, The system of Example 16, wherein the scaling map is associated with a first state and an additional scaling map is associated with a second state, the at least one processing device being further configured to: determine that the subject is in the first state; and select the scaling map in response to determining that the subject is in the first state.

In an Example 21, the system of Example 20, wherein the first state corresponds to a first value of a state parameter, the state parameter comprising at least one of a position of the subject, a posture of the subject, an activity of the subject, and a location of the subject.

In an Example 22, the system of Example 16, wherein the first scaled value and the second scaled value are determined by applying a linear normalization based on the first scaling vector and the second scaling vector, respectively.

In an Example 23, the system of Example 16, wherein the at least one processing device is configured to predict the physiological event by applying a predictive model that was created based on one or more observations associated with a reference location, and wherein the at least one processing device is configured to create the scaling map by: determining a linear normalization associated with a plurality of signal characteristic values, the plurality of signal characteristic values comprising at least the first value of the signal characteristic and the second value of the signal characteristic; identifying a location of the plurality of locations that corresponds to the reference location; and projecting the linear normalization into a reference position space corresponding to the reference location.

In an Example 24, the system of Example 16, wherein the at least one processing device is configured to create the scaling map based on at least a third physiological signal and a fourth physiological signal, wherein the third physiological signal corresponds to the first location, and wherein the fourth physiological signal corresponds to the second location.

In an Example 25, a method for facilitating predicting a physiological event, wherein the prediction is determined by at least one processing device implementing a predictive algorithm configured to predict the physiological event based on a physiological parameter measurement derived from at least two physiological signals, the method comprising: receiving, from a first sensor disposed at a first location, a first physiological signal produced by a source, wherein the source is associated with a body part of a subject; receiving, from a second sensor disposed at a second location, a second physiological signal produced by the source; determining a first value of a signal characteristic, the first value of the signal characteristic corresponding to the first physiological signal; determining a second value of the signal characteristic, the second value of the signal characteristic corresponding to the second physiological signal; creating, based on the first and second signal characteristics, a scaling map, the scaling map comprising a plurality of scaling vectors, each of the plurality of scaling vectors corresponding to one of the plurality of locations, each scaling vector comprising at least one signal characteristic correction value; receiving, from the first sensor, a third physiological signal; receiving, from the second sensor, a fourth physiological signal; determining a third value of the signal characteristic, the third value of the signal characteristic corresponding to the third physiological signal; determining a fourth value of the signal characteristic, the fourth value of the signal characteristic corresponding to the fourth physiological signal; accessing the scaling map; determining a scaled third value and a scaled fourth value based on a first scaling vector and a second scaling vector, respectively, the first scaling vector corresponding to the first location and the second scaling vector corresponding to the second location; and predicting a physiological event based on the scaled third value of the signal characteristic and the scaled fourth value of the signal characteristic.

In an Example 26, the method of Example 25, wherein the first sensor comprises an accelerometer configured to sense an acceleration signal produced by the source.

In an Example 27, the method of Example 25, wherein the source is a heart of the subject, and wherein the acceleration signal corresponds to one or more heart sounds.

In an Example 28, the method of Example 25, wherein the signal characteristic comprises at least one of an amplitude, a phase, and a frequency.

In an Example 29, the method of Example 25, wherein the scaling map is associated with a first state, and wherein the at least one processing device is further configured to create an additional scaling map, wherein the additional scaling map is associated with a second state.

In an Example 30, one or more computer-readable media having computer-executable instructions embodied thereon that, when executed by at least one processing device, are configured to cause the at least one processing device to perform a method of facilitating physiological monitoring, the method comprising: receiving, from at least one sensor at a first location, a first physiological signal produced by a source, wherein the source is associated with a body part of a subject; receiving, from the at least one sensor at a second location, a second physiological signal produced by the source; determining a first value of a signal characteristic, the first value of the signal characteristic corresponding to the first physiological signal; determining a second value of the signal characteristic, the second value of the signal characteristic corresponding to the second physiological signal; accessing a scaling map, the scaling map comprising a plurality of scaling vectors, each of the plurality of scaling vectors corresponding to one of a plurality of locations, the plurality of locations comprising the first location and the second location, and each scaling vector comprising at least one signal characteristic correction value; determining a scaled first value and a scaled second value based on a first scaling vector and a second scaling vector, respectively, the first scaling vector corresponding to the first location and the second scaling vector corresponding to the second location; and predicting a physiological event based on the scaled first value of the signal characteristic and the scaled second value of the signal characteristic.

In an Example 31, the media of Example 30, wherein the first sensor comprises an accelerometer configured to sense an acceleration signal produced by the source.

In an Example 32, the media of Example 30, wherein the source is a heart of the subject, and wherein the acceleration signal corresponds to one or more heart sounds.

In an Example 33, the media of Example 30, wherein the signal characteristic comprises at least one of an amplitude, a phase, and a frequency.

In an Example 34, the media of Example 30, wherein the at least one processing device is configured to create the scaling map based on at least a third physiological signal and a fourth physiological signal, wherein the third physiological signal corresponds to the first location, and wherein the fourth physiological signal corresponds to the second location.

In an Example 35, the media of Example 30, wherein the scaling map is associated with a first state and an additional scaling map is associated with a second state, the method further comprising: determining that the subject is in the first state; and selecting the scaling map in response to determining that the subject is in the first state.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
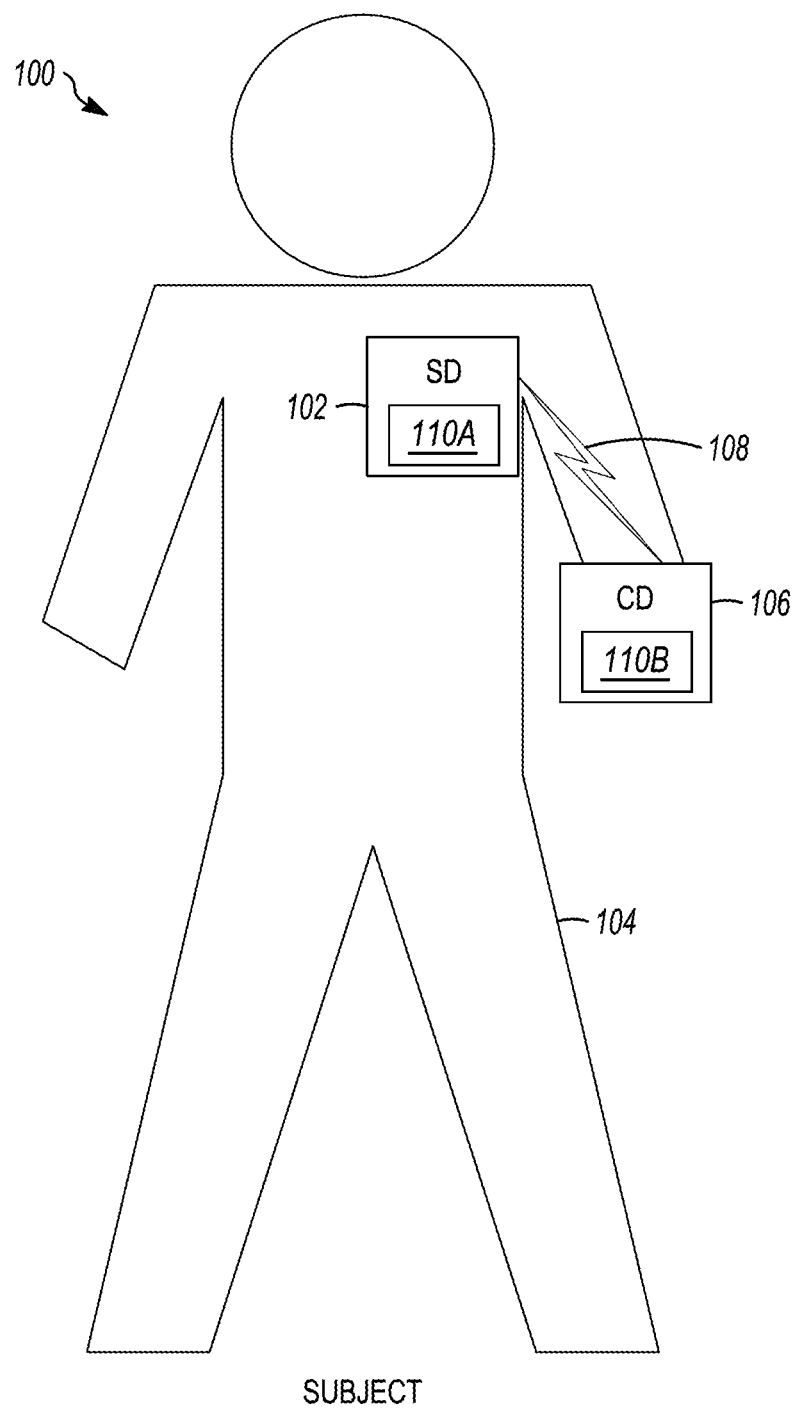
FIG. 1 is a schematic diagram of an illustrative medical system, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

A "heart sound," as the term is used herein, includes audible and inaudible mechanical vibrations caused by cardiac activity that can be sensed with an accelerometer. Accordingly, when a mechanical sensor such as an accelerometer is used to sense the heart sounds, the scope of energy included in the sensed "acoustic signal" extends to energies associated with such mechanical vibrations. Unless noted otherwise, S1 refers to the first heart sound, S2 refers to the second heart sound, S3 refers to the third heart sound, and S4 refers to the fourth heart sounds, each as a heart sound type, or as one or more occurrences of the corresponding type heart sounds, depending on the context. A "heart beat" includes a cardiac cycle. An "S3 beat" includes a cardiac cycle during which S3 is detected. An "S3 index," also referred to as an "S3 ratio," includes a ratio of the number of the S3 beats to the number of the total heart hearts, both detected during the same time period.

S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. Data associated with any number of different heart sounds may be used to diagnose, predict, characterize, control treatment of, and/or otherwise analyze any number of different aspects of conditions, illnesses, states of being, and/or the like.

FIG. 1 shows an illustrative imaging system 100, in accordance with embodiments of the disclosure. As shown in FIG. 1, the imaging system 100 includes a sensing device (SD) 102 configured to be positioned adjacent (e.g., on) the body of a subject 104. In embodiments, the imaging system 100 may include a computational device (CD) 106, which is communicatively coupled to the SD 102 via a communication link 108. The subject 104 may be a human, a dog, a pig, and/or any other animal. For example, in embodiments, the subject 104 may be a human patient. According to embodiments, the CD 106 may be, be similar to, include, be included within, or be integrated with the SD 102.

In embodiments, the SD 102 and/or the CD 106 may be used to sense and/or monitor any number of a variety of physiological, device, subjective, and/or environmental parameters associated with the subject 104, using electrical, mechanical, and/or chemical means. For example, the SD 102 and/or the CD 106 may include sensors or circuitry for detecting sounds, respiratory system signals, cardiac system signals, and/or signals related to patient activity. To do so, the SD 102 and/or the CD 106 may include sensing components such as, for example, one or more surface electrodes configured to obtain an electrocardiogram (ECG), one or more accelerometers configured to detect motion associated with the subject 104, one or more respiratory sensors configured to obtain respiration information, one or more environmental sensors configured to obtain information about the external environment (e.g., temperature, air quality, humidity, carbon monoxide level, oxygen level, barometric pressure, light intensity, sound, and/or the like) surrounding the subject 104, and/or the like. In embodiments, the SD 102 and/or the CD 106 may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

In embodiments, the sounds capable of being detected by the SD 102 and/or the CD 106 may be, but are not limited to, heart sounds, sounds produced by an organ other than the heart, sounds produced by a thumper and/or the like. To detect sounds, the SD 102 and/or the CD 106 may include one or more sensors 110A and 110B, respectively. That is, the SD 102 and/or the CD 106 may be configured to use the sensors 110A and/or 110B to generate heart sound data, sound data from organs other than the heart (e.g., respiration data), and/or other physiological data. Heart sound data includes information associated with heart sounds such as, for example, identifications of heart sounds, a heart sound signal extracted from an acceleration signal, classifications of heart sounds, statistics or other derived information associated with heart sounds, physiological parameters determined based on heart sounds, and/or the like. Similarly, respiration data includes information associated with respiration such as, for example, identifications of respiratory events and/or stages, a respiration signal extracted from an acceleration (or heart sound) signal, classifications of respiratory events, statistics or other derived information associated with respiration, physiological parameters determined based on respiration information, and/or the like.

In embodiments, the sensors 110A, 110B may be configured to generate an acceleration signal and/or acceleration data, which may include the acceleration signal, information derived from the acceleration signal, and/or the like. In embodiments, the acceleration data includes acceleration measurements associated with movement of the SD 102 and/or the CD 106. In embodiments, the sensors 110A, 110B may be, or include, any accelerometer known in the art of and configured to generate measurements associated with its motion. An "accelerometer," as used herein, may be, or include, any type of accelerometer, gyroscope, magnetometer, inertial measurement unit (IMU), and/or any other type of sensor or combination of sensors configured to measure changes in acceleration, angular velocity, and/or the like. In embodiments, the accelerometers 110A, 110B may include multiple accelerometers and may be disposed in multiple, different locations on the subject 104.

In embodiments, most smartphones currently include accelerometers configured to generate acceleration data associated with three-dimensional movement of the smartphone (which, in embodiments, may be the SD 102 and/or the CD 106). The inventors have discovered that conventional smartphone accelerometers may be used for detecting heart sounds when the smartphone is positioned in contact with a subject's body in a target region. According to embodiments, a target region is a region in which heart sound signals may be obtained using an accelerometer. That is, for example, when a subject is lying on his or her back, a target region may include the subject's torso or a portion thereof (e.g., the chest); whereas, when a subject is lying on his or her stomach, the target region may include the subject's back. A target location may include any location within a target region and/or a specified location within a target location. According to various embodiments, the target region of a subject may be identified by analyzing acceleration data obtained from the accelerometer to determine, for a given location, whether heart sounds are able to be detected using the accelerometer.

Additionally or alternatively, sensors and associated circuitry (e.g., the sensors 110A, 110B) may be incorporated in connection with the SD 102 and/or CD 106 for detecting one or more body movement or body posture and/or position related signals. For example, the accelerometer 110 and/or GPS device may be employed to detect patient activity, patient location, body orientation, and/or torso position. Derived parameters may also be monitored using the SD 102 and/or CD 106.

The SD 102 and/or the CD 106 may be configured to automatically gather data, gather data upon request (e.g., input provided by the subject, a clinician, another device, and/or the like), and/or any number of various combinations and/or modifications thereof. The SD 102 may be configured to store data related to the physiological, device, environmental, and/or subjective parameters and/or transmit the data to any number of other devices (e.g., CD 106) in the system 100.

In embodiments, the SD 102 and/or the CD 106 may be configured to analyze data and/or act upon the analyzed data. For example, the SD 102 and/or the CD 106 may be configured to image a body part of the subject 104 based on the monitored data, predict a physiological event, facilitate a physiological intervention, modify therapy, perform additional monitoring, and/or provide alarm indications based on the analysis of the data. In embodiments, the SD 102 and/or the CD 106 may be any type of device having data analysis capabilities such as, for example, a smartphone, a tablet, a notebook, or other portable computing device. In embodiments, the CD 106 may be a separate device from the SD 102. Alternatively, the SD 102 may be integrated into the CD 106. Additionally or alternatively, while one SD 102 and one CD 106 are depicted in FIG. 1, embodiments may include more than one SD 102 and/or more than one CD 106. In embodiments, the monitoring and/or analyzing functions described above may be allocated between the SD 102 and the CD 106. For example, the SD 102 may primarily perform the monitoring functions described above and the CD 106 may primarily perform the analyzing functions describe above.

In embodiments, the SD 102 and/or the CD 106 may be configured to provide therapy. To do so, the SD 102 and/or the CD 106 may include any number of different therapy components such as, for example, a defibrillation component, a drug delivery component, a neurostimulation component, a neuromodulation component, a temperature regulation component, and/or the like. In embodiments, the SD 102 and/or the CD 106 may include limited functionality, e.g., defibrillation shock delivery and communication capabilities, with arrhythmia detection, classification and/or therapy command/control being performed by a separate device. For example, the SD 102 and/or the CD 106 may be configured to communicate with implanted stimulation devices, infusion devices, and/or the like, to facilitate delivery of therapy.

The SD 102 and/or the CD 106 may be, include, or be included in a medical device (external and/or implanted) that may be configured to deliver therapy. Therapy may be provided automatically and/or upon request (e.g., an input by the subject 104, a clinician, another device or process, and/or the like). The SD 102 and/or the CD 106 may be programmable in that various characteristics of their sensing, therapy (e.g., duration and interval), and/or communication may be altered by communication between the SD 102 and the CD 106 and/or other components of the system 100.

According to embodiments, the SD 102 and/or the CD 106 may include any type of medical device, any number of different components of an implantable or external medical system, a mobile device, a mobile device accessory, and/or the like. That is, for example, the SD 102 and/or the CD 106 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104. In various embodiments, the SD 102 and/or the CD 106 may include both defibrillation and pacing/CRT capabilities (e.g., a CRT-D device). In embodiments, the SD 102 and/or the CD 106 may be implanted subcutaneously within an implantation location or pocket in the patient's chest or abdomen and may be configured to monitor (e.g., sense and/or record) physiological parameters associated with the patient's heart. In embodiments, the SD and/or the CD 106 may be an implantable cardiac monitor (ICM) (e.g., an implantable diagnostic monitor (IDM), an implantable loop recorder (ILR), etc.) configured to record physiological parameters such as, for example, one or more cardiac electrical signals, heart sounds, heart rate, blood pressure measurements, oxygen saturations, and/or the like.

In embodiments, the SD and/or the CD 106 may include a mobile device accessory such as, for example, a device having an electrocardiogram (ECG) module. An ECG module may include any hardware, software, and/or firmware configured to generate ECG data (e.g., ECG measurements, estimated ECG measurements, information about ECG measurements, information derived from ECG measurements, etc.). The SD and/or the CD 106 may include, for example, an ECG sensor assembly such as, for example, the Kardia Mobile device available from AliveCor, of Mountain View, Calif., USA, which works in conjunction with an app that may be considered to be part of the ECG module. In embodiments, the SD 102 and/or the CD 106 may include, for example, a smart watch such as, for example, a Fitbit, available from Fitbit, Inc., of San Francisco, Calif., USA. In this manner, the ECG module may include components of a CD 106 and/or the SD 102.

In various embodiments, the SD 102 and/or the CD 106 may be a device that is configured to be portable with the subject 104, e.g., by being integrated into a vest, belt, harness, sticker; placed into a pocket, a purse, or a backpack; carried in the subject's hand; and/or the like, or otherwise operatively (and/or physically) coupled to the subject 104. The SD 102 and/or the CD 106 may be configured to monitor (e.g., sense and/or record) physiological parameters associated with the subject 104 and/or provide therapy to the subject 104. For example, the SD 102 and/or the CD 106 may be, or include, a wearable cardiac defibrillator (WCD) such as a vest that includes one or more defibrillation electrodes In embodiments, the SD 102 may be operatively coupled to the subject 104, and the SD 102 and the CD 106 may be configured to communicate with one another over the communication link 108. In embodiments, the communication link 108 may be, or include, a wired link (e.g., a link accomplished via a physical connection) and/or a wireless communication link such as, for example, a short-range radio link, such as Bluetooth, IEEE 802.11, near-field communication (NFC), WiFi, a proprietary wireless protocol, and/or the like. The term "communication link" may refer to an ability to communicate some type of information in at least one direction between at least two devices, and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the SD 102 and the CD 106, and/or indirect communications that travel between the SD 102 and the CD 106 via at least one other device (e.g., a repeater, router, hub, and/or the like). The communication link 108 may facilitate uni-directional and/or bi-directional communication between the SD 102 and the CD 106. Data and/or control signals may be transmitted between the SD 102 and the CD 106 to coordinate the functions of the SD 102 and/or the CD 106. In embodiments, subject data may be downloaded from one or more of the SD 102 and the CD 106 periodically or on command. The clinician and/or the subject may communicate with the SD 102 and/or the CD 106, for example, to acquire subject data or to initiate, terminate and/or modify sensing and/or computation.

The illustrative cardiac monitoring system 100 shown in FIG. 1 is not intended to suggest any limitation as to the scope of use or functionality of embodiments of the present disclosure. The illustrative cardiac monitoring system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein.

Figure 2:
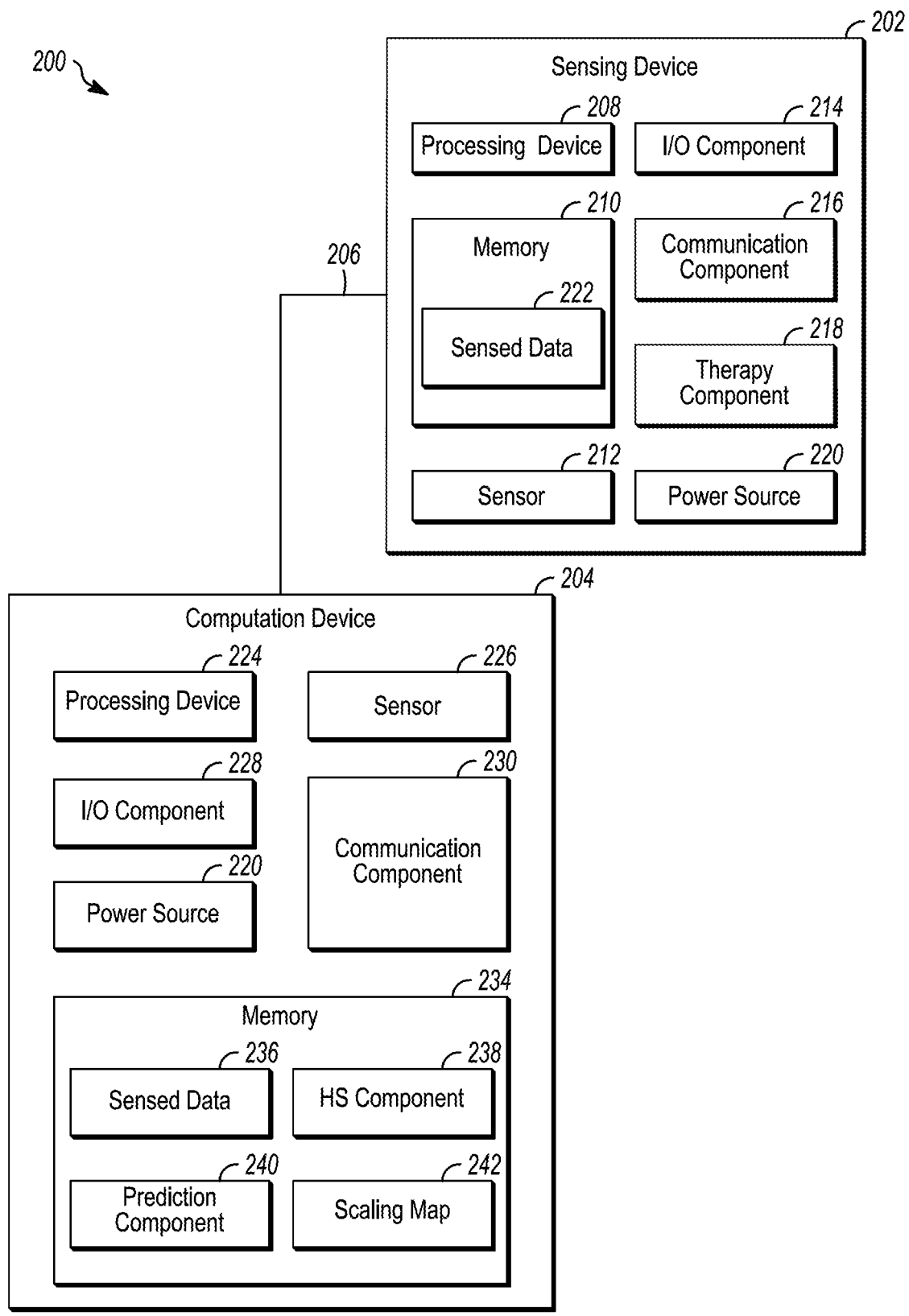
FIG. 2 is a block diagram depicting an illustrative operating environment, in accordance with embodiments of the subject matter disclosed herein.

FIG. 2 is a block diagram depicting an illustrative operating environment 200, in accordance with embodiments of the subject matter disclosed herein. According to embodiments, the operating environment 200 may be, be similar to, include, be included in, or otherwise correspond to the system 100 depicted in FIG. 1. As shown in FIG. 2, the illustrative operating environment 200 includes a sensing device (SD) 202 configured to communicate with a computation device (CD) 204 via a communication link 206. In embodiments, the operating environment 200 may include the SD 202 without including a CD 204, include the CD 204 without including the SD 202, and/or include another device. Additionally or alternatively, the operating environment 200 may include more than one SD 202 and/or more than one CD 204. According to embodiments, the SD 202 may be, be similar to, include, or be included in the SD 102 depicted in FIG. 1; the CD 204 may be, be similar to, include, or be included in the CD 106 depicted in FIG. 1; and, the communication link 206 may be, be similar to, include, or be included in the communication links 108 depicted in FIG. 1.

According to embodiments illustrated in FIG. 2, the SD 202 includes a processing device 208, a memory 210, a sensor 212, an input/output (I/O) component 214, a communication component 216, a therapy component 218, and/or a power source 220.

The processing device 208 may include, for example, a processing unit, a pulse generator, a controller, a microcontroller, and/or the like. The processing device 208 may be any arrangement of electronic circuits, electronic components, processors, program components and/or the like configured to store and/or execute programming instructions, to direct the operation of the other functional components of the SD 202 (e.g., to direct the sensor 212 to sense sounds), to perform processing on any sounds sensed by the sensor 212, to direct the therapy component 218 to provide a therapy, and/or the like, and may be implemented, for example, in the form of any combination of hardware, software, and/or firmware.

In embodiments, the processing device 208 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the processing device 208 may include a processing unit configured to communicate with memory 210 to execute computer-executable instructions stored in the memory 210. Although the processing device 208 is referred to herein in the singular, the processing device 208 may be implemented in multiple instances, distributed across multiple sensing devices, instantiated within multiple virtual machines, and/or the like.

The processing device 208 may also be configured to store information in the memory 210 and/or access information from the memory 210. For example, the processing device 208 may be configured to store data obtained by the sensor 212 as sensed data 222 in memory 210.

In embodiments, the memory 210 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

Computer-executable instructions stored on memory 210 may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

In embodiments, the sensor 212 may sense, at one or more times and/or at one or more locations, physiological signals (e.g., signals including and/or representing various sounds, physiological and/or environmental parameters), which may then be saved as sensed data 222 on memory 210 and/or transmitted to the CD 204. In embodiments where heart sounds are sensed by the sensor 212, the sensed data 222 may include information associated with heart sounds such as, for example, identifications of heart sounds, classifications of heart sounds, statistics associated with heart sounds, physiological parameters derived from heart sound data, and/or the like. In embodiments, the sensor 212 may be, include, or be included within an accelerometer.

The environmental parameters may include particulates, ultraviolet light, volatile organic compounds, and/or the like in the environment. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like.

The physiological signals sensed by the sensor 212 may be associated with a subject (e.g., the subject 104) by travelling through tissue of a subject and then sensed by the sensor 212. The physiological signals associated with a subject may be used by the SD 202 and/or the CD 204 to facilitate predicting a physiological event associated with a subject. Additionally or alternatively, location data indicative of the location of the sensor 212 may be saved as sensed data 222 and/or transmitted to the CD 204. While one sensor 212 is depicted as being included in the SD 202, the SD 202 may include multiple sensors 212 that are arranged on, potentially, different locations of a subject (e.g., the subject 104).

To sense various sounds, physiological and/or environmental parameters, the sensor 212 may include temperature sensors (e.g., thermocouples or thermistors), barometers, acoustic sensors, pressure sensors, optical sensors, motion or impact sensors (e.g., accelerometers, inertial measuring units (IMUs)), strain sensors, Doppler systems, chemical sensors, ultrasound sensors, and/or the like, in any number of various types of configurations. The foregoing sensors allow the SD 202 to be capable of sensing and recording parameters such as, for example, organ and non-organ sounds, patient movement, posture, respiratory cycles, and/or the like. The output from the sensor 212 may be used in classification, therapy selection, trigger event detection, physiological event prediction, physiological intervention facilitation, and/or the like.

The I/O component 214 may include and/or be coupled to a user interface configured to present information to a user or receive indication from a user. For example, the I/O component 214 may include and/or be coupled to a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like. In embodiments, the I/O component 214 may be used to present and/or provide an indication of any of the data sensed and/or produced by the SD 202.

The communication component 216 may be configured to communicate (i.e., send and/or receive signals) with the CD 204 and/or other devices. In embodiments, the communication component 216 may be configured to send sensed data 222 to the CD 204 in response to sensing one or more sounds produced by a body part. Additionally or alternatively, the communication component 216 may be configured to receive signals from the CD 204 to, for example, supplement the sensed data 222 sensed by the sensor 212. The communication component 216 may include, for example, circuits, program components, and one or more transmitters and/or receivers for communicating wirelessly with one or more other devices such as, for example, the CD 204. According to various embodiments, the communication component 216 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 216 may include any combination of hardware, software, and/or firmware configured to facilitate establishing, maintaining, and using any number of communication links.

The therapy component 218 may be configured to delivery therapy in response to one or more sensed and/or derived signals. In embodiments, the therapy component 218 may include any number of different therapy components such as, for example, a drug delivery component, an inhaler component, a nebulizer component, defibrillation component, a neurostimulation component, a neuromodulation component, a temperature regulation component, and/or the like.

The power source 220 provides electrical power to the other operative components (e.g., the processing device 208, the memory 210, the sensor 212, the I/O component 214, the communication component 216, and/or the therapy component 218), and may be any type of power source suitable for providing the desired performance and/or longevity requirements of the SD 202. In various embodiments, the power source 220 may include one or more batteries, which may be rechargeable (e.g., using an external energy source). For example, in embodiments, the CD 204 and/or another device may be used to charge the power source 220, transfer power to the power source 220 and/or the like. The power source 220 may include one or more capacitors, energy conversion mechanisms, and/or the like. Additionally or alternatively, the power source 220 may harvest energy from a subject (e.g., the subject 104) (e.g. motion, heat, biochemical) and/or from the environment (e.g. electromagnetic). Additionally or alternatively, the power source 220 may harvest energy from an energy source connected to the body, for example, a shoe may receive energy from impact and send the received energy to a power source 220 of the SD 202.

As shown in FIG. 2, the CD 204 includes a processing device 224, a sensor 226, an I/O component 228, a communication component 230, a power source 232, and/or a memory 234.

The processing device 224 may include, for example, a processing unit, a pulse generator, a controller, a microcontroller, and/or the like. The processing device 224 may be any arrangement of electronic circuits, electronic components, processors, program components and/or the like configured to store and/or execute programming instructions, to direct the operation of the other functional components of the CD 204, to image a body part of a subject using sounds, and/or perform any number of other functions such as, for example, perform ECG detection, EEG detection, EMG detection, arrhythmia detection, respiratory functionality detection, and/or classification algorithms, to store physiologic data obtained by the sensor 226 as sensed data 236 on the memory 234, and/or the like, and may be implemented, for example, in the form of any combination of hardware, software, and/or firmware.

In embodiments, the processing device 224 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the processing device 224 may include a processing unit configured to communicate with memory to execute computer-executable instructions stored in the memory. Although the processing device 224 is referred to herein in the singular, the processing device 224 may be implemented in multiple instances, distributed across multiple computing devices, instantiated within multiple virtual machines, and/or the like.

The processing device 224 may also be configured to store information in the memory 234 and/or access information from the memory 234. The processing device 224 may execute instructions and perform desired tasks as specified by computer-executable instructions stored in the memory 234. In embodiments, for example, the processing device 224 may be configured to instantiate, by executing instructions stored in the memory 234, a heart sound (HS) component 238, a source analyzer 240, a prediction component 242, and/or the like. Additionally or alternatively, the processing device 224 may store any sensed data 236 sensed by the sensor 226 in the memory 234. In embodiments, the processing device 224 may store any sensed data 222 transmitted to the CD 204 from the SD 202 as sensed data 236 in the memory 236. Additionally or alternatively, if the sensed data 236 is transferred from the CD 204 to another device, the processing device 224 may be configured to erase the sensed data 236 from the CD 204 to free-up storage space on the memory 234.

The sensor 226 may sense various sounds, physiological and/or environmental parameters, which may then be saved as sensed data 236. The sounds may be produced by an organ (e.g., heart sounds) and/or may be produced by a device. In embodiments where heart sounds are sensed by the sensor 226, the sensed data 236 may include information associated with heart sounds such as, for example, identifications of heart sounds, classifications of heart sounds, statistics associated with heart sounds, physiological parameters derived from heart sound data, and/or the like.

The environmental parameters may include particulates, ultraviolet light, volatile organic compounds, and/or the like in the environment. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like.

The sounds sensed by the sensor 226 may be associated with a subject (e.g., the subject 104) by travelling through tissue of a subject and then sensed by the sensor 226. The sounds associated with a subject may be used by the CD 204 to image a body part of a subject. For example, the sounds travelling through a subject will be attenuated, which can then be used to create a scaling map 238, which may be used to normalize signal characteristics associated with physiological signals sensed by the sensor 212 and/or 226, to facilitate predicting a physiological event.

Additionally or alternatively, location data indicative of the location of the sensor 226 may be saved as sensed data 236. While one sensor 226 is depicted as being included in the CD 204, the CD 204 may include multiple sensors 226 that are configured, for example, to be arranged on, potentially, different locations of a subject (e.g., the subject 104).

To sense the one or more sounds, environmental parameters and/or physiological parameters, the sensor 226 may include temperature sensors (e.g., thermocouples or thermistors), barometers, acoustic sensors, pressure sensors, optical sensors, motion or impact sensors (e.g., accelerometers, gyroscopes, inertial measuring units (IMUs)), strain sensors, Doppler systems, chemical sensors, ultrasound sensors, and/or the like, in any number of various types of configurations. In embodiments, the sensed data 236 of the sensor 226 may supplement the sensed data 222 of the sensor 212. For example, the sensor 226 may have a location that is different than the location of the sensor 212. As such, a single source may produce sensed data 236 that is different than the sensed data 222 due to the locations of the sensors 212, 226 and, therefore, different attenuations of the signals being sensed.

The I/O component 228 may include and/or be coupled to a user interface configured to present information to a user or receive indication from a user. For example, the I/O component 228 may include and/or be coupled to a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, a volatile compound release depot, and/or the like. In embodiments, the I/O component 228 may be used to present and/or provide an indication of any of the data sensed and/or produced by the CD 204 and/or the SD 202. For example, the I/O component 228 may be used to present an a representation of an output of a predictive algorithm configured to predict a physiological event (e.g., a predicted value, an alert, an alarm, etc.), a representation of a physiological signal, and/or the like. In embodiments, the I/O component 228 may include one or more visual indicators (e.g., single-color LED lights, multi-color LED lights, a flexible digital display device, and/or the like) configured to provide information to a user (e.g., by illuminating, flashing, displaying data, etc.). Additionally or alternatively, the I/O component 228 may be used to control therapy provided by the SD 202.

The communication component 230 may be configured to communicate (i.e., send and/or receive signals) with the SD 202 and/or any other device. Additionally or alternatively, the communication component 230 may facilitate receiving the sensed data 222 from the SD 202 and/or transmit the sensed data 236 from the CD 204 to the SD 202 and/or to another device for processing and/or storage.

In embodiments, the communication component 230 may include, for example, circuits, program components, and one or more transmitters and/or receivers for communicating wirelessly with one or more other devices such as, for example, the SD 202. According to various embodiments, the communication component 230 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 230 may include any combination of hardware, software, and/or firmware configured to facilitate establishing, maintaining, and using any number of communication links.

The power source 232 provides electrical power to the other operative components (e.g., the processing device 224, the sensor 226, the I/O component 228, the communication component 230, and/or the memory 234), and may be any type of power source suitable for providing the desired performance and/or longevity requirements of the CD 204. In various embodiments, the power source 232 may include one or more batteries, which may be rechargeable (e.g., using an external energy source). The power source 232 may include one or more capacitors, energy conversion mechanisms, and/or the like. Additionally or alternatively, the power source 232 may harvest energy from a subject (e.g., the subject 104) (e.g. motion, heat, biochemical) and/or from the environment (e.g. electromagnetic). Additionally or alternatively, the power source 232 may harvest energy from an energy source connected to the body, for example, a shoe may receive energy from impact and send the received energy to a power source 232 of the CD 204. In embodiments, the power source 220 may transfer power to the power source 232 (or vice versa) using a wireless or non-wireless connection (e.g., via conduction, induction, radio-frequency, etc.).

In embodiments, the memory 234 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The memory 234 may store instructions that, when executed by the processing device 224 cause methods and processes to be performed by the CD 204. That is, for example, the processing device 224 may process instructions and/or data stored in the memory 234 to facilitate detection and/or analysis of organ sounds (e.g., heart sounds) and/or non-organ sounds (e.g., produced by the thumper 214), prediction of physiological events, and/or the like.

For example, the processing device 224 may instantiate (e.g., from the memory 234) a HS component 238. In embodiments, the HS component 238 may be configured to generate heart sound data 236 from the data collected by the sensor 226 (and/or the sensed data 222 collected by the sensor 212) by performing any number of different processes such as, for example, filtering, interpolating, and/or the like. In embodiments, the HS component 238 may be configured to standardize the acceleration data before the processing device further processes it. For example, the HS component 238 may be configured to standardize sampling rates, normalize physiological signal characteristic values, and/or the like.

Many conventional accelerometers are configured to take measurements in response to a demand for acceleration data and, often, those measurements are taken using sample rates that are dynamically determined based on the movement of the accelerometer and/or the like. Accordingly, acceleration data often is not generated using a fixed sampling rate. Thus, the HS component 238 may be configured to standardize the acceleration data—that is, to perform a process on the acceleration data that changes it into standardized acceleration data, which is acceleration data that has been modified to estimate what the acceleration data would be if it had been generated using a fixed sampling rate. In embodiments, the HS component 238 may be configured to perform a data interpolation process on the acceleration data to generate standardized acceleration data. The interpolation may be configured to generate standardized acceleration data based on templates, internal characteristics of the acceleration data, known information, and/or the like.

According to embodiments, the HS component 238 may be configured to generate heart sound data that can be stored as sensed data 236, based on the acceleration data, by performing, in addition to or in lieu of other techniques discussed herein, a noise reduction process on the standardized acceleration data. In embodiments, performing the noise reduction process on the standardized acceleration data may include performing at least one of: spectral filtering (e.g., by attenuating specified frequencies, frequency bands, etc.), bandpass filtering (e.g., by attenuating frequency bands above and/or below specified thresholds), high pass filtering (e.g., by attenuating frequencies below a specified threshold to remove DC offsets), and/or the like. Attenuating components of a signal, as described herein, may include removing, suppressing, transforming, or otherwise attenuating the component of the signal as is understood by those having skill in the relevant arts. In this manner, noise reduction may be performed by rejecting signal values that are not likely to include heart sound information.

According to embodiments, the HS component 238 may be configured to normalize values of a signal characteristic across multiple measurement devices, times, locations, and/or the like. For example, in embodiments, the HS component 238 may be configured to receive, from one or more medical devices (which may include separate devices, connected and/or integrated sensors, and/or the like), a first and second physiological signal, where the first physiological signal corresponds to a first measurement location and the second physiological signal corresponds to a second measurement location. In embodiments, the sensor (or sensors) may include one or more accelerometers configured to sense acceleration signals produced by a source. The source may be a heart of a subject, where the acceleration signals may correspond to heart sounds.

The HS component 238 may be configured to determine a first value of a signal characteristic, the first value of the signal characteristic corresponding to the first physiological signal; and determine a second value of the signal characteristic, the second value of the signal characteristic corresponding to the second physiological signal. According to embodiments, the signal characteristic may include an amplitude, a phase, a frequency, and/or the like.

According to embodiments, the HS component 238 may be further configured to generate and/or access a scaling map, the scaling map including a number of scaling vectors, each of the scaling vectors corresponding to one of a number of locations, the locations including the first location and the second location, and each scaling vector including at least one signal characteristic correction value. The HS component 238 may be configured to determine a scaled first value and a scaled second value based on a first scaling vector and a second scaling vector, respectively, the first scaling vector corresponding to the first location and the second scaling vector corresponding to the second location.

In embodiments, the scaling map may be associated with a first state and an additional scaling map may be associated with a second state (and any number of additional scaling maps may be associated with any number of additional states). The HS component 238 may be configured to determine which state the subject is in; and select the appropriate scaling map in response to determining which state the subject is in. In embodiments, the state may correspond to a value of a state parameter, the state parameter including a value indicating a position of the subject, a posture of the subject, an activity of the subject, a location of the subject, and/or the like.

According to embodiments, scaled values may be determined by applying a linear normalization based on the corresponding scaling vectors. In embodiments, the scaling vectors may be configured to normalize signal characteristic values in a generalized space. In embodiments, the scaling vectors may be configured to normalize signal characteristic values with respect to a reference location. That is, for example, the computation device 204 may be configured to predict a physiological event by applying a predictive model that was created based on one or more observations associated with a reference location. In embodiments of that situation, the HS component 238 may be configured to create the scaling map by determining a linear normalization associated with a number of signal characteristic values, identifying a location that corresponds to the reference location; and projecting the linear normalization into a reference position space corresponding to the reference location.

In embodiments, for example, a frequency band and/or threshold corresponding to heart sounds of a subject may be determined using information from the CD 204, the SD 202, and/or the like, and used to filter an acceleration signal (and/or standardized acceleration signal) to attenuate acceleration data that is not associated with heart sounds. It has been discovered, for example, that components of an acceleration signal having a frequency above approximately 200 Hertz are generally not associated with heart sounds. Thus, in embodiments, the HS component 238 may be configured to attenuate the component of the accelerometer signal not associated with heart sounds such as, for example, by attenuating accelerometer data having frequencies above approximately 200 Hertz. In some embodiments, this may be the only filtering process performed on the standardized acceleration signal, while, in other embodiments, other filtering process may be performed in addition to, or in lieu of, this frequency filtering. For example, in embodiments, copies of the accelerometer signal may be band-pass filtered by filters having a band-pass width of 5 Hertz, 10 Hertz, 15 Hertz, 20 Hertz and/or the like. In these embodiments, multiple data bands may be derived from the acceleration signals. Each of these data bands may be used to generate a system of equations used to image a part of subject as explained below.

Additionally or alternatively, the processing device 224 may instantiate (e.g., from the memory 234) a prediction component 240. In embodiments, the prediction component 240 may be configured to determine, based on the sensed data 236, a likelihood of an occurrence of a physiological event, which may be referred to herein as "predicting an event" and/or the like. In embodiments, for example, the prediction component 240 may be configured to predict an occurrence of a next heart beat (e.g., by predicting a time at which the next heart beat will occur), a cardiac failure, a loss of consciousness, and/or the like.

The prediction component 242 may be configured to implement an algorithm to predict a physiological event associated with a particular body part, which the sound at least partially propagates through, based on the sensed data 236. In predicting a physiological event, the prediction component 242 may be configured to obtain and/or store a set of information (e.g., sensed data 236) that may be analyzed using one or more adjudication algorithms to predict and/or classify a cardiac episode, audit the effectiveness of a therapy regimen, and/or the like. According to embodiments, prediction data (e.g., classifications, characterization data, sensed data, etc.) can be stored in an adjudication database. In some examples, the characterization data may be sent to a medical device (e.g., sensing device 202 and/or computation device 204) to be stored, displayed, and/or otherwise acted upon. Once a classification (e.g., an arrhythmia classification) has been generated for a particular physiological event or a group of events, it may be possible to provide patients and/or clinicians with many different types of reports related to the event data. It may also be possible for the system to analyze the classifications and/or characterization data to provide programming recommendations for a medical device where certain conditions are present. It may also be possible to query the adjudication database for many different types of information that may be useful to clinicians, researchers, regulators, and/or the like.

In embodiments, the prediction component 242 may utilize information collected by components of a medical system (which may include, e.g., the system 100 depicted in FIG. 1, the operating environment 200 depicted in FIG. 2, etc.), as well as information from other relevant sources, to analyze data related to a subject, and provide predictive assessments of the subject's well-being. In performing this analysis, the prediction component 242 may utilize data collected from a variety of sources, include patient specific physiological and subjective data, medical and historical records (e.g., lab test results, histories of illnesses, etc., drugs currently and previously administered, etc.), information related to population trends, and/or the like.

In embodiments, the prediction component 242 may provide a diagnosis of subject health status and predicted trend based on present and recent historical data. For example, the prediction component 242 may perform probabilistic calculations using currently-collected information combined with regularly-collected historical information to predict subject health degradation. In embodiments, the prediction component 242 may conduct pre-evaluation of the incoming data stream combined with subject historical information and information from subjects with similar disease states. The pre-evaluation system may be based on data derived from working clinical practices and the records of outcomes. The derived data may be processed in a neural network, fuzzy logic system, or equivalent system to reflect the clinical practice. Further, the prediction component 242 may provide means for periodic processing of present and historical data to yield a multidimensional health state indication along with disease trend prediction, next phase of disease progression co-morbidities, and/or inferences about what other possible diseases may be involved. The prediction component 242 may also integrate data collected from internal and external devices to optimize management of overall patient health.

The prediction component 242 may perform any number of different deterministic and probabilistic calculations. In embodiments, the analysis component 332 may include machine-learning capabilities. For example, the prediction component 242 may be implemented via a neural network (or equivalent) system. The prediction component 242 may be partially trained (i.e., the prediction component 242 may be implemented with a given set of preset values and then learn as the advanced patient management system functions) or untrained (i.e., the prediction component 242 may be initiated with no preset values and must learn from scratch as the advanced patient management system functions). In embodiments, the prediction component 242 may continue to learn and adjust as the medical system functions (i.e., in real time), or the prediction component 242 may remain at a given level of learning and only advanced to a higher level of understanding when manually allowed to do so.

The prediction component 242 may be configured to use various algorithms and mathematical modeling such as, for example, trend and statistical analysis, data mining, pattern recognition, cluster analysis, neural networks fuzzy logic, and/or the like. The prediction component 242 may perform deterministic and probabilistic calculations. Deterministic calculations include algorithms for which a clear correlation is known between the data analyzed and a given outcome. Additionally, using the prediction component 242, a bifurcated analysis may be performed for diseases exhibiting similar symptoms. As progressive quantities of data are collected and the understanding of a given disease state advances, disease analysis may be refined such as, for example, where a former singular classification may split into two or more sub-classes.

Any number of various components of the operating environment 200 depicted in FIG. 2 may be communicatively coupled via the communication link 206. The communication link 206 may provide for communications between and among various components of the operating environment 200, such as the SD 202 and the CD 204. The communication link 206 may be, be similar to, include, or be included in the communication link 108 depicted in FIG. 1, and/or any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The communication link 306 may include a combination of multiple networks, which may be wired and/or wireless.

The illustrative operating environment shown in FIG. 2 is not intended to suggest any limitation as to the scope of use or functionality of embodiments of the present disclosure. The illustrative operating environment 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3A:
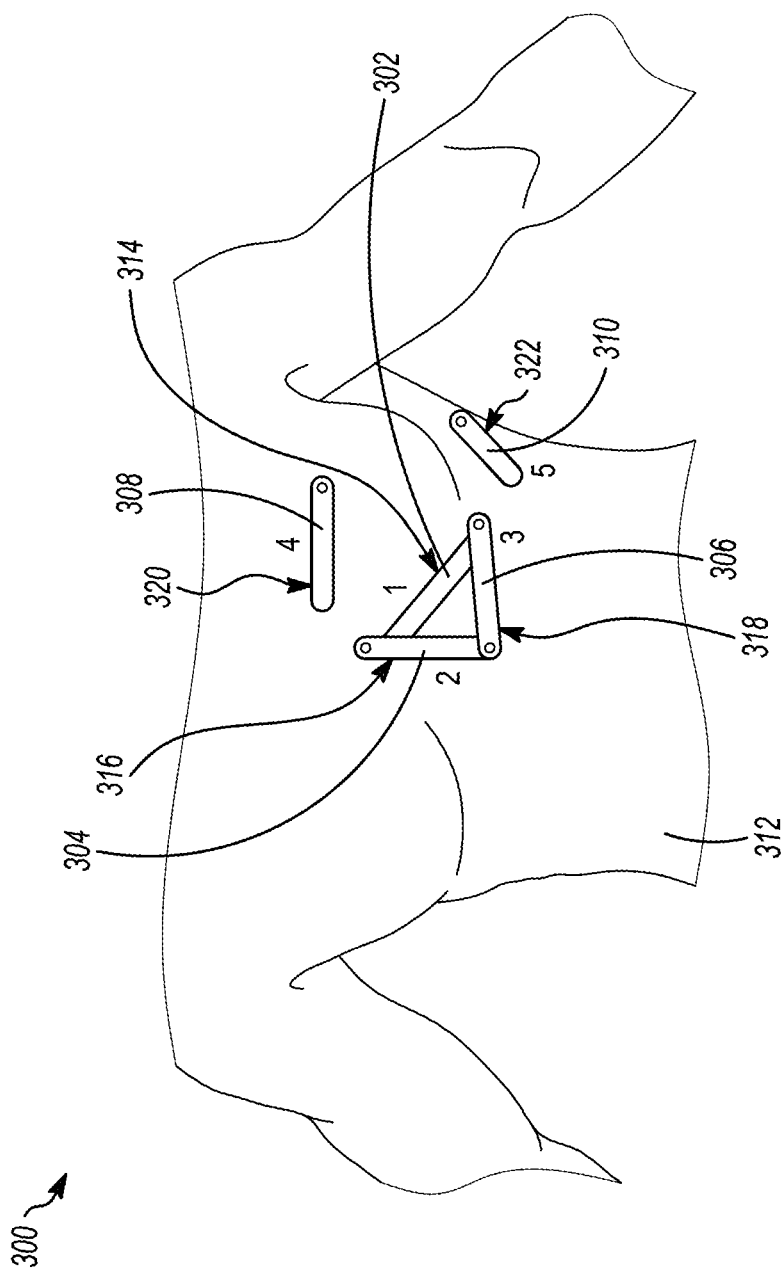
FIG. 3A is a schematic depiction of an illustrative medical system and subject, in accordance with embodiments of the subject matter disclosed herein.

FIG. 3A depicts an illustrative medical system 300 having a number of medical devices 302, 304, 306, 308, and 310 disposed on or in a subject 312, in accordance with embodiments of the subject matter disclosed herein. According to embodiments, the medical system 300 may be, be similar to, include, be included within, or otherwise correspond to, the medical system 100 depicted in FIG. 1 and/or the operating environment 200 depicted in FIG. 2.

As shown in FIG. 3A, the medical devices 302, 304, 306, 308, and 310 may be separate medical devices such as, for example, individual sensing devices (e.g., the SD 102 depicted in FIG. 1), computation devices (e.g., the CD 106 depicted in FIG. 1), and/or the like. In embodiments, the medical devices 302, 304, 306, 308, and 310 may represent a fewer number of devices than are illustrated (e.g., one, two, three, or four) disposed at different locations at different times. That is, for example, the medical devices 302, 304, 306, 308, and 310 may represent a single medical device being placed on the surface (e.g., skin) of the subject 312 at different (e.g., sequential) times. In any case, the medical devices 302, 304, 306, 308, and 310 may each include a sensor (not shown) configured to sense physiological signals such as, for example, sounds (e.g., heart sounds, respiration sounds, etc.) at corresponding measurement locations 314, 316, 318, 320, and 322.

Embodiments of the medical system 300 may be configured to facilitate collecting physiological signals (e.g., including heart sound data) from multiple measurement locations, determining a signal characteristic associated with each physiological signal, and normalizing the values of the signal characteristic across the locations. In embodiments, the medical devices 302, 304, 306, 308, and 310 (e.g., wearable devices, implanted devices, calibration devices, smartphones, etc.) may be used to collect physiological signals from multiple locations. A patient-specific scaling map may be created and applied to subsequently-obtained physiological signals. In this manner, differences in physiological signal characteristics due to differences in measurement location may be mitigated and/or removed. In this manner, embodiments of the medical system described herein may facilitate increasing the accuracy of heart sound data collected from multiple locations.

Normalization of signal characteristic values may be achieved using one or more scaling maps. A scaling map may be any collection of information that can be used to scale one or more signal characteristics of physiological signals. For example, in embodiments, a scaling map may include a matrix representing scaling vectors determined based on a set of physiological signals obtained at various measurement locations. Each scaling vector may be location and/or time specific, and may include, for example, a measurement location (e.g., x, y, and z coordinates), a scaling value, and a time value (e.g., an indication of an absolute time or a relative time). A scaling map may be created by obtaining physiological signals corresponding to a number of measurement locations—e.g., by disposing a number of medical devices in, on, or adjacent to the subject at those locations, or by disposing a single medical device in the measurement locations sequentially, obtaining physiological signals at each.

The scaling value may be determined using a linear normalization (e.g., a linear damping function). In embodiments, for example, a scaling value in generalized space for a particular location at a particular time point (e.g., time sample) may be determined by dividing the value of the signal characteristic at that location and time by a sum of the signal characteristic values across all measurement locations and/or time points within a measurement window. In embodiments, each measurement window may include a specified number of samples over time period (e.g., 110 samples, 220 samples, 440 samples, etc.). The samples may be evenly spaced, temporally, within the measurement window.

The generalized scaling values may be projected into a space associated with a position vector corresponding to a particular measurement location to obtain a scaled value that represents a measurement obtained at that location. For example, embodiments of predictive algorithms often are developed using empirical data obtained from medical devices disposed in, on or adjacent to a number of subjects. An example of such a predictive algorithm that may be implemented, in accordance with embodiments of the subject matter disclosed herein is the Heart Logic™ predictive engine available from Boston Scientific, of Marlborough, Mass., USA. The portions of the Heart Logic™ algorithm that include heart sounds were developed using measurements from implanted medical devices corresponding, at least approximately, to the location 320 at which the medical device 308 is disposed in FIG. 3. Accordingly, scaling vectors developed for producing scaled signal characteristic values for use with the Heart Logic™ algorithm may be determined by projecting the general-space normalized values into a reference space (e.g., the vector space associated with a reference location—the location 320 of medical device 308). In embodiments, projecting a general scaling vector into a reference space may include multiplying the general scaling vector by the scaling vector associated with a sensor disposed in (at least approximately) the reference location. According to embodiments, any number of other arrangements of medical devices, measurement locations, and/or the like may be utilized in implementations, and may be utilized with any number of different predictive algorithms.

Scaling maps may be dynamic—that is, for example, a scaling map may be updated based on signal characteristics of a set of physiological signals (e.g., each time a new set of physiological signals is obtained, the scaling map may be updated). In this manner, a dynamic scaling map may be configured to facilitate producing accurate scaled values even though attenuation of physiological signals may change due to, for example, changes in subject activity, posture, location, and/or the like. In embodiments, the medical system 300 may be configured to create and/or utilize any number of scaling maps, each of which may include any number of scaling vectors. That is, for example, two different scaling maps may correspond, respectively, to two different states. A state may refer to a state of the subject, an environmental state, a device state, and/or the like. For example, in embodiments, a state may refer to a particular type of subject activity, posture, geographic location, and/or the like. A processing device may be configured to determine a current state and to select, based on the current state, the corresponding scaling map. In this manner, physiological signals (e.g., heart sounds) may be dynamically monitored with a consistent level of accuracy even though relative positions of medical devices may change, and/or the like.

Figure 3B:
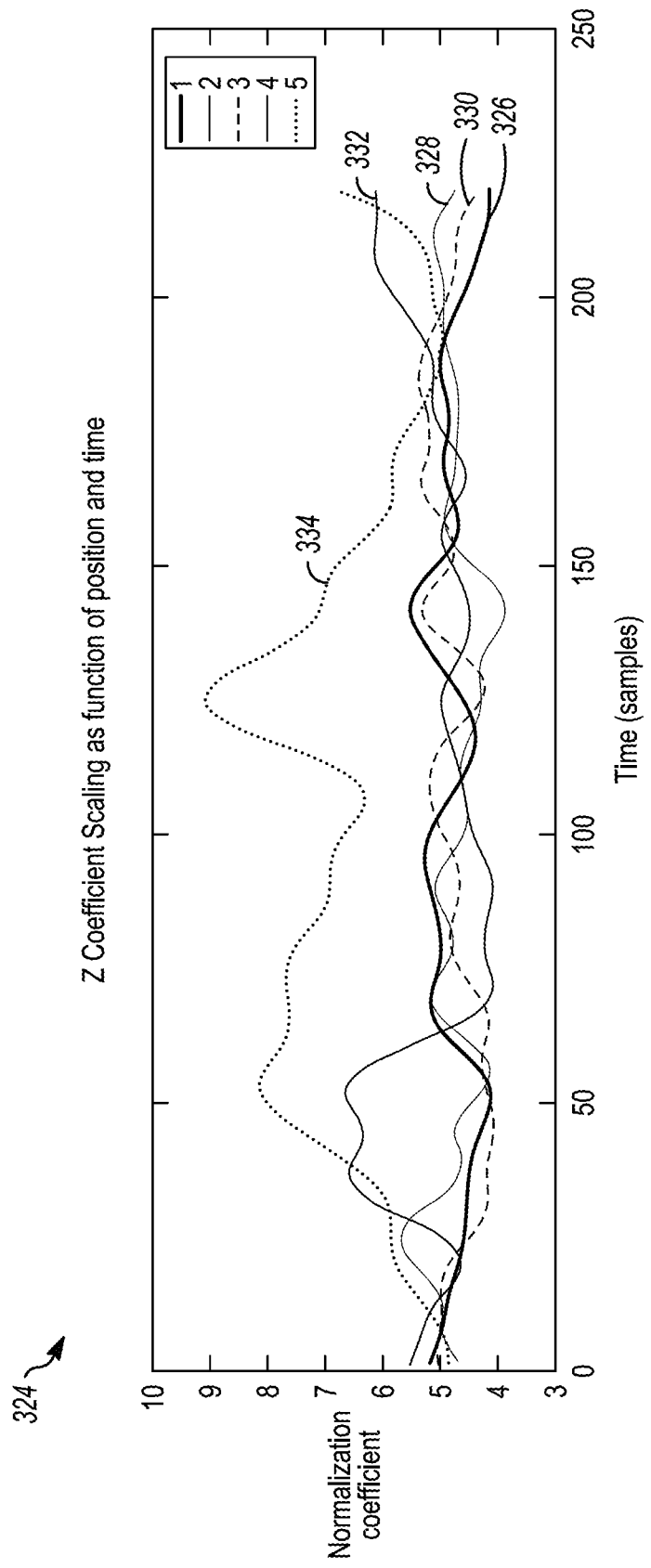
FIG. 3B is a graph depicting an illustrative representation of scaling vectors, in accordance with embodiments of the subject matter disclosed herein.

In embodiments, as shown in the illustrative graph 324 of FIG. 3B, scaling vectors may be stored and/or represented as waveforms (e.g., signals). As shown, for example, a sampling window may correspond to 220 sampled points, and the scaling vectors for each may include 220 scaled values—one for each location and time point. A continuous function may be determined for each location 314, 316, 318, 320, and 322 depicted in FIG. 3A, and represented by a curve 326, 328, 330, 332, and 334, respectively. In embodiments, a source analyzer may normalize observed physiological signal characteristics by applying, to a determined signal characteristic, the continuous function, by applying individual scaling values, and/or the like. According to embodiments, any number of different ways of storing, organizing, and/or representing scaling vectors may be utilized.

The illustrative medical system 300 shown in FIGS. 3A and 3B is not intended to suggest any limitation as to the scope of use or functionality of embodiments of the present disclosure. The illustrative medical system 300 should not be interpreted as having any dependency or requirement related to any single component or combination of components illustrated therein. Additionally, various components depicted in FIGS. 3A and 3B may be, in embodiments, integrated with various ones of the other components depicted therein (and/or components not illustrated), all of which are considered to be within the ambit of the subject matter disclosed herein.

Figure 4:
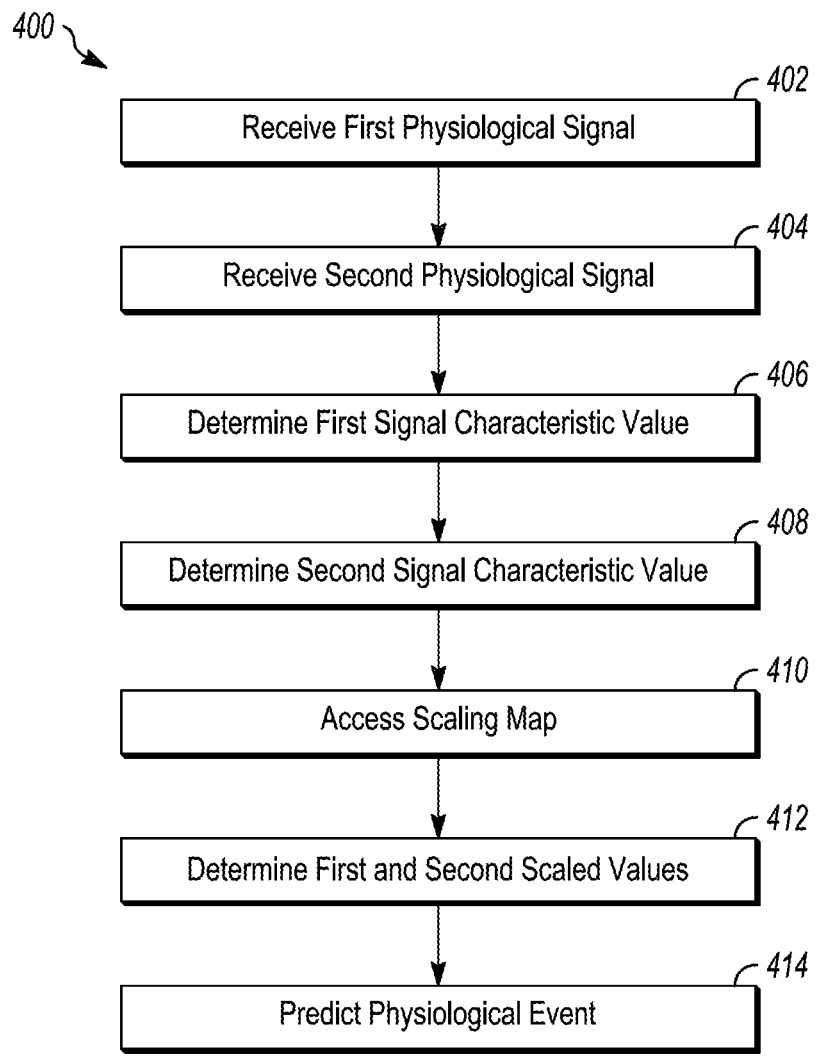
FIG. 4 is a flow diagram of an illustrative method for facilitating physiological monitoring, in accordance with embodiments of the subject matter disclosed herein.

FIG. 4 is a flow diagram depicting an illustrative method 400 for facilitating physiological monitoring, in accordance with embodiments of the present disclosure. According to embodiments, the method 400 may be performed by any number of different aspects of components of the system 100 depicted in FIG. 1, the operating environment 200 depicted in FIG. 2, and/or the system 300 depicted in FIG. 3. Embodiments of the method 400 include receiving (block 402), from at least one sensor at a first location, a first physiological signal produced by a source, wherein the source is associated with a body part of a subject; and receiving (block 404), from the at least one sensor at a second location, a second physiological signal produced by the source. The method 400 may further include determining (block 406) a first value of a signal characteristic, the first value of the signal characteristic corresponding to the first physiological signal; and determining (block 408) a second value of the signal characteristic, the second value of the signal characteristic corresponding to the second physiological signal.

Embodiments of the method 400 further include accessing (block 410) a scaling map, the scaling map including a number of scaling vectors, each of the scaling vectors corresponding to one of a number of locations, the locations including the first location and the second location, and each scaling vector including at least one signal characteristic correction value. In embodiments, the method 400 further includes determining (block 412) a scaled first value and a scaled second value based on a first scaling vector and a second scaling vector, respectively, the first scaling vector corresponding to the first location and the second scaling vector corresponding to the second location; and predicting (block 414) a physiological event based on the scaled first value of the signal characteristic and the scaled second value of the signal characteristic.

Figure 5:
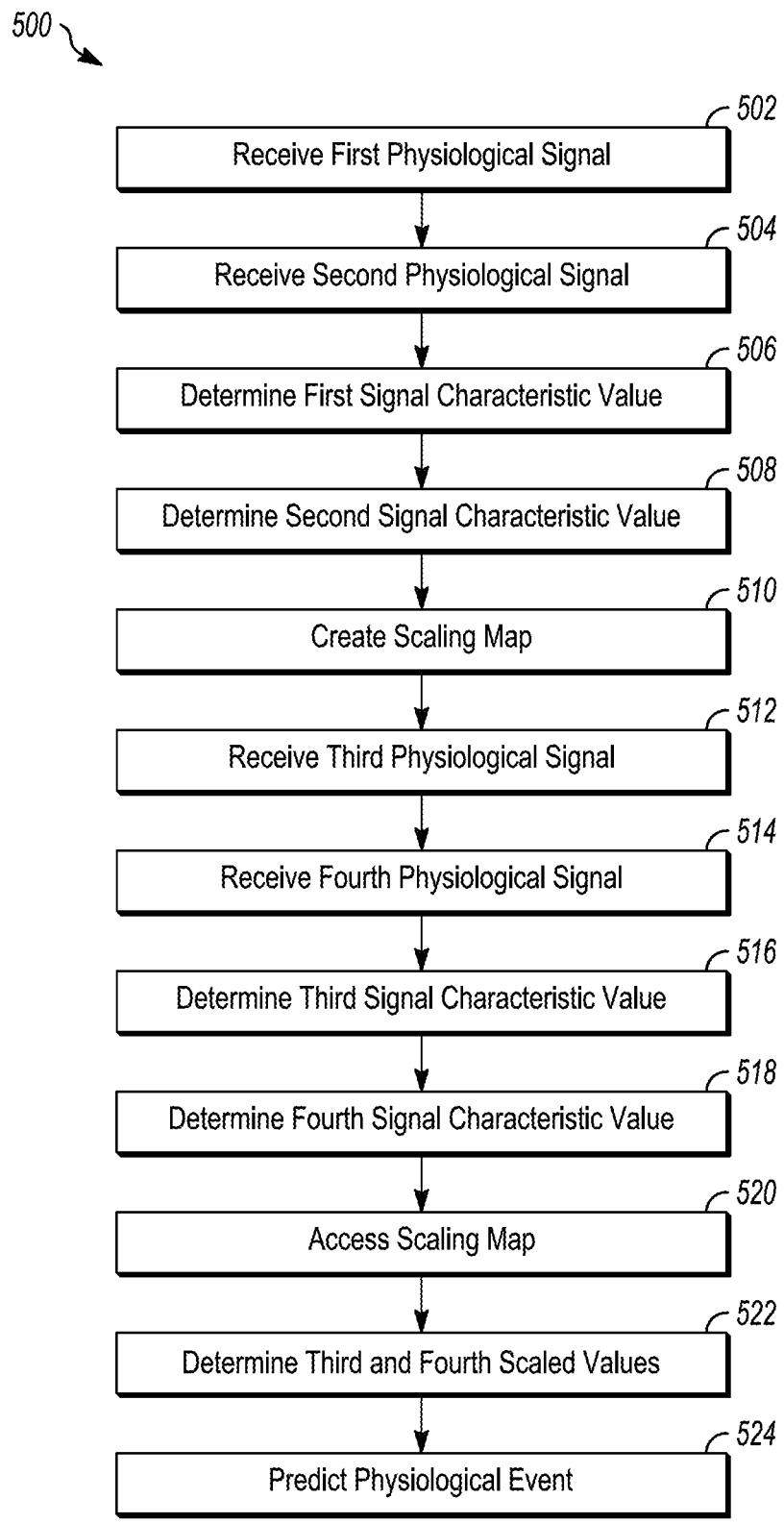
FIG. 5 is another flow diagram depicting an illustrative method for facilitating physiological monitoring, in accordance with embodiments of the subject matter disclosed herein.

FIG. 5 is another flow diagram depicting an illustrative method 500 for facilitating physiological monitoring, in accordance with embodiments of the present disclosure. According to embodiments, the method 500 may be performed by any number of different aspects of components of the system 100 depicted in FIG. 1, the operating environment 200 depicted in FIG. 2, and/or the system 300 depicted in FIG. 3. Embodiments of the method 500 include receiving (block 502), from a first sensor disposed at a first location, a first physiological signal produced by a source, wherein the source is associated with a body part of a subject; and receiving (block 504), from a second sensor disposed at a second location, a second physiological signal produced by the source.

According to embodiments, the method 500 includes determining (block 506) a first value of a signal characteristic, the first value of the signal characteristic corresponding to the first physiological signal; and determining (block 508) a second value of the signal characteristic, the second value of the signal characteristic corresponding to the second physiological signal. The method 500 may include creating (block 510), based on the first and second signal characteristics, a scaling map, the scaling map including a number of scaling vectors, each of the scaling vectors corresponding to one of the locations, and each scaling vector including at least one signal characteristic correction value.

The method 500 may further include receiving (block 512), from the first sensor, a third physiological signal; receiving (block 514), from the second sensor, a fourth physiological signal; determining (block 516) a third value of the signal characteristic, the third value of the signal characteristic corresponding to the third physiological signal; and determining (block 518) a fourth value of the signal characteristic, the fourth value of the signal characteristic corresponding to the fourth physiological signal. In embodiments, the method 500 further includes accessing (block 520) the scaling map; determining (block 522) a scaled third value and a scaled fourth value based on a first scaling vector and a second scaling vector, respectively, the first scaling vector corresponding to the first location and the second scaling vector corresponding to the second location; and predicting (block 524) a physiological event based on the scaled third value of the signal characteristic and the scaled fourth value of the signal characteristic.

Various modifications and additions can be made to the exemplary embodiments discussed without departing from the scope of the presently disclosed subject matter. For example, while the embodiments described above refer to particular features, the scope of this disclosure also includes embodiments having different combinations of features and embodiments that do not include all of the described features. Accordingly, the scope of the subject matter disclosed herein is intended to embrace all such alternatives, modifications, and variations as fall within the scope of the claims, together with all equivalents thereof.

We claim:

1. A system for facilitating physiological monitoring, the system comprising:
   a first sensor configured to sense a first physiological signal representing heart sounds, at a first location within a chest region or within a back region;
   a second sensor configured to sense a second physiological signal representing the heart sounds, at a second location within the chest region or within the back region; and
   at least one processing device communicatively coupled to the first and second sensors, the at least one processing device configured to:
      receive the first and second physiological signals;
      determine a first value of a signal characteristic, the first value of the signal characteristic corresponding to the first physiological signal;
      determine a second value of the signal characteristic, the second value of the signal characteristic corresponding to the second physiological signal;
      access a scaling map, the scaling map comprising a plurality of scaling vectors, each of the plurality of scaling vectors corresponding to one of a plurality of locations, the plurality of locations comprising the first location and the second location, and each scaling vector comprising at least one signal characteristic correction value;
      determine a scaled first value and a scaled second value based on a first scaling vector and a second scaling vector, respectively, the first scaling vector corresponding to the first location and the second scaling vector corresponding to the second location; and
      predict a physiological event based on the scaled first value of the signal characteristic and the scaled second value of the signal characteristic.

2. The system of claim 1, wherein the first and second sensors comprise an accelerometer configured to sense the heart sounds.

3. The system of claim 1, wherein the signal characteristic is amplitude, wherein the scaled first value is a scaled amplitude of the first physiological signal, wherein the scaled second value is a scaled amplitude of the second physiological signal.

4. The system of claim 1, wherein the scaling map is associated with a first state and an additional scaling map is associated with a second state, the at least one processing device being further configured to:
   determine that a subject is in the first state; and
   select the scaling map in response to determining that the subject is in the first state.

5. The system of claim 4, wherein the first state corresponds to a first value of a state parameter, the state parameter comprising at least one of a position of the subject, a posture of the subject, an activity of the subject, and a location of the subject.

6. The system of claim 1, wherein the first scaled value and the second scaled value are determined by applying a linear normalization based on the first scaling vector and the second scaling vector, respectively.

7. The system of claim 1, wherein the at least one processing device is configured to predict the physiological event by applying a predictive model that was created based on one or more observations associated with a reference location, and wherein the at least one processing device is configured to create the scaling map by:
determining a linear normalization associated with a plurality of signal characteristic values, the plurality of signal characteristic values comprising at least the first value of the signal characteristic and the second value of the signal characteristic;
identifying a location of the plurality of locations that corresponds to the reference location; and
projecting the linear normalization into a reference position space corresponding to the reference location.

8. The system of claim 1, wherein the at least one processing device is configured to create the scaling map based on at least a third physiological signal and a fourth physiological signal, wherein the third physiological signal corresponds to the first location, and wherein the fourth physiological signal corresponds to the second location.

9. The system of claim 1, wherein the heart sounds comprise S1, S2, S3, and S4 heart sounds.

10. The system of claim 1, wherein the first physiological signal and the second physiological signal are accelerometer signals, wherein the at least one processing device is configured to attenuate acceleration data not associated with the heart sounds.

11. The system of claim 10, wherein the at least one processing device is configured to attenuate acceleration data having a frequency above 200 Hertz.

12. A system comprising:
a first acceleration sensor, at a first location within a chest or back region, configured to generate a first signal indicative of heart sounds;
a second acceleration sensor, at a second location within the chest or the back region, configured to generate a second signal indicative of the heart sounds; and
a microprocessor communicatively coupled to the first and second acceleration sensors, the microprocessor configured to:
determine a first amplitude of the first signal,
determine a second amplitude of the second signal,
access a scaling map, the scaling map comprising a first scaling vector corresponding to the first location and a second scaling vector corresponding to the second location,
calculate a scaled first amplitude based on the first scaling vector,
calculate a scaled second amplitude based on the second scaling vector, and
predict a physiological event based on the scaled first amplitude and on the scaled second amplitude.

13. The system of claim 12, wherein the first physiological signal and the second physiological signal are accelerometer signals, wherein the at least one processing device is configured to attenuate acceleration data not associated with the heart sounds.

14. The system of claim 13, wherein the at least one processing device is configured to attenuate acceleration data having a frequency above 200 Hertz.

15. The system of claim 12, wherein the first sensor is part of an implantable medical device.

16. The system of claim 15, wherein second sensor is part of a device configured to be positioned externally to a subject's body.

17. One or more computer-readable media having computer-executable instructions embodied thereon that, when executed by at least one processing device, are configured to cause the at least one processing device to perform a method of facilitating physiological monitoring, the method comprising:
receiving, from at least one sensor at a first location, a first physiological signal representing heart sounds;
receiving, from the at least one sensor at a second location, a second physiological signal representing the heart sounds;
determining a first amplitude of the first physiological signal;
determining a second amplitude of the second physiological signal;
accessing a scaling map, the scaling map comprising a plurality of scaling vectors, each of the plurality of scaling vectors corresponding to one of a plurality of locations, the plurality of locations comprising the first location and the second location, and each scaling vector comprising at least one signal characteristic correction value;
determining a scaled first amplitude of the first physiological signal and a scaled second amplitude of the second physiological signal based on a first scaling vector of the scaling map and a second scaling vector of the scaling map, respectively, the first scaling vector corresponding to the first location and the second scaling vector corresponding to the second location; and
predicting a physiological event based on the scaled first amplitude of the first physiological signal and the scaled second amplitude of the second physiological signal and the scaled second.

18. The media of claim 17, wherein the at least one sensor comprises an accelerometer configured to sense the heart sounds.

19. The media of claim 17, wherein the at least one processing device is configured to create the scaling map based on at least a third physiological signal and a fourth physiological signal, wherein the third physiological signal corresponds to the first location, and wherein the fourth physiological signal corresponds to the second location.

20. The media of claim 17, wherein the scaling map is associated with a first state and an additional scaling map is associated with a second state, the method further comprising:
determining that a subject is in the first state; and
selecting the scaling map in response to determining that the subject is in the first state.

* * * * *